United States Patent
Russo et al.

(10) Patent No.: US 7,252,740 B2
(45) Date of Patent: Aug. 7, 2007

(54) (PER) FLUOROPOLYETHER CARBOXYLIC ACIDS AND USE THEREOF FOR THE OLEO-REPELLENT PAPER SIZING

(75) Inventors: Antonio Russo, Milan (IT); Claudio Tonelli, Milan (IT); Mario Visca, Alessandria (IT)

(73) Assignee: Solvay Solexis, S.p.A., Milan (IT)

( * ) Notice: Subject to any disclaimer, the term of this patent is extended or adjusted under 35 U.S.C. 154(b) by 392 days.

(21) Appl. No.: 10/859,580

(22) Filed: Jun. 3, 2004

(65) Prior Publication Data

US 2005/0004395 A1 Jan. 6, 2005

(30) Foreign Application Priority Data

Jun. 3, 2003 (IT) .......................... MI2003A1104

(51) Int. Cl.
*D21H 25/00* (2006.01)
(52) U.S. Cl. ............................... 162/164.3; 106/287.28
(58) Field of Classification Search ............... 562/602, 562/605; 527/411, 284; 162/164.3; 106/287.28
See application file for complete search history.

(56) References Cited

U.S. PATENT DOCUMENTS

| | | | |
|---|---|---|---|
| 3,810,874 A | 5/1974 | Mitsch et al. | |
| 4,997,873 A * | 3/1991 | Suling et al. | ............... 524/458 |
| 5,543,567 A | 8/1996 | Bierschenk et al. | ........ 562/582 |
| 5,557,012 A | 9/1996 | Bierschenk et al. | ........ 562/582 |
| 5,718,833 A | 2/1998 | Yamamoto et al. | ...... 252/62.52 |
| 5,738,802 A | 4/1998 | Yamamoto et al. | ...... 252/62.56 |
| 5,785,882 A | 7/1998 | Yamamoto et al. | ...... 252/62.52 |
| 6,221,434 B1 * | 4/2001 | Visca et al. | ............... 427/393.4 |
| 6,395,848 B1 | 5/2002 | Morgan et al. | ............. 526/214 |
| 6,429,258 B1 | 8/2002 | Morgan et al. | ............. 524/804 |

FOREIGN PATENT DOCUMENTS

| | | |
|---|---|---|
| EP | 1 006 168 A1 | 6/2000 |
| EP | 1 273 704 A1 | 1/2003 |
| EP | 1 327 649 A2 | 7/2003 |
| EP | 1 371 676 A1 | 12/2003 |

\* cited by examiner

*Primary Examiner*—Karl Puttlitz
(74) *Attorney, Agent, or Firm*—Arent Fox, LLP

(57) ABSTRACT

Carboxylic acids comprising perfluoropolyether chains, of formula:

$$T_1-CFW_1-O-R_f-CFW_2-T_2 \quad (I)$$

wherein $T_1$, $T_2$, equal to or different from each other, are selected from the group formed of $-CH_2-B-Y-(COOH)_n$, $-CH(CF_3)O-Y(COOH)_n$, $-F$, $-CF_3$, $-C_2F_5$, $-(C_2F_4)Cl$, wherein $B=-O-$ or $-S-$; $Y=C_1-C_{20}$ alkylene chain, n=1-4; with the proviso that at least one of the two end groups $T_1$, $T_2$ be $-CH_2-B-Y-(COOH)_n$, $-CH(CF_3)O-Y(COOH)_n$; $W_1$, $W_2$, equal to or different from each other, are $-F$ or $-CF_3$; $R_f$ is a (per)fluoropolyoxyalkylene chain formed of one or more repeating units, statistically distributed along the chain, having a number average molecular weight in the range 500-10,000.

9 Claims, No Drawings

(PER) FLUOROPOLYETHER CARBOXYLIC ACIDS AND USE THEREOF FOR THE OLEO-REPELLENT PAPER SIZING

The present invention relates to carboxylic acids comprising perfluoropolyether chains and to their salts, to the process for the preparation thereof and to the aqueous compositions containing them capable to confer oleo-repellence to various artificial or natural substrata, especially paper.

More specifically, the present invention relates to carboxylic acids comprising perfluoropolyether chains and salts thereof capable to confer to the paper an oleo-repellence capable to pass the severe tests indicated hereinafter.

It is known to render oleo-repellent various substrata and in particular paper products used for the packaging of vegetable oil-based fats, of products such as coffee, chocolate and also for the packaging of foods having a high fat content as meats, chips, hamburgers, popcorns, foods to be cooked in microwave oven, and pet food. For these uses, the substrata for the packaging, in particular paper, are sized with products which confer a resistance to oils and to fats capable to pass the application tests used by food package producers.

The oleo-repellence is usually evaluated with the Kit Test (TAPPI 557 method) in terms of resistance of the paper sized to the penetration of the oil contained in hydrocarbon or in hydrocarbon mixtures drops having a progressively decreasing surface tension, maintained in contact for 15 seconds with the paper specimen. Drops formed of mixtures of castor oil, toluene and heptane in various proportions are generally used.

The oleo-repellence values obtained with the kit Test are however an index of the only surface activity of the oleo-repellent agent (fluorinated compound) and often they have a poor correlation with the real performance in terms of protective barrier to oils and fats, in normal use conditions of paper packages where there are prolonged contact times with foods, and in severe use conditions due to the temperature (heating of food packages in microwave ovens) and to mechanical stresses due to creasing to obtain the manufactured article.

On this ground users utilise a series of performance tests considered more adherent to practical applications, such as for example:

Ralston Crease Test (RP-2 Test)

The resistance properties to the oil penetration in antigrease papers for pet-food packaging are evaluated. The % of the surface stained by the coloured oil is determined. The acceptability limit of the sample is 2% of the stained surface.

Resistance Test to Oleic Acid

The resistance to oleic acid is evaluated at 60° C. for 2 hours. The test passes (positive) when the paper is not stained and does not show halos (% of stained surface=0).

Resistance Test to Fat Acid Mixtures

It is evaluated the resistance at 60° C. for 10 minutes of the paper sized with five fat acid mixtures (A*), (B*), (C*), (D*), (E*). The mixture (A*) containing 20% by weight of fat acid, diluted in 80% by weight of castor oil, having a low aggressive power, is used to discriminate the low performance levels; the compositions of the fat acid mixtures (B*), C(*), D(*) and E(*) have a rising aggressive power and represent respectively the fat acid compositions of the olive oil, animal lard, butter and coconut oil. For each mixture the test is considered positive if the paper does not show halos either on the side sized or least of all on the opposite side and the test result is expressed with the letter of the test mixture preceding that which penetrates through the specimen.

Of course (E*) represents the best oleo-repellence value one can obtain. Depending on the type of the use of the oleo-repellent paper, even values lower than (E*) can be acceptable.

Resistance Test to Trementine (Turpentine test TAPPI T454)

The resistance to trementine for 30 minutes is evaluated. The test passes (positive) when the paper is not stained.

Resistance Test to Exausted Seed-oil (Hot Mazola Oil Test)

This test evaluates the resistance to the exhausted seed-oil at 100° C. for 20 minutes of paper sized having a Kit Test value from 3 to 6. The test passes (positive) when within 20 minutes the stain of the absorbed oil is not visible.

Aqueous polyurethane compositions containing perfluoropolyether structures are known, see for example. European patent application No. 02.014.155, and the use thereof in the oleo-repellent paper sizing. Said polyurethanes are capable to confer oleo-repellence to paper and to satisfy the tests indicated in said patent application among which the Ralston Crease test. Said tests are generally used by paper-mills to verify if the paper obtained in the wet-end treatment of the cellulose pulp or in the surface one of the size-press, is capable to satisfy the user require-ments. In this patent application it is not said if these aqueous polyurethane compositions are able to satisfy the most severe tests used by the paper mills, as, for example, the resistance tests to fat acid mixtures and to trementine.

Tests carried out by the Applicant have shown that papers sized with said polyurethanes do not pass most of said tests. To pass all the above tests it is necessary to use a remarkable amount of polyurethanes that implies a cost rising hardly bearable by paper mills.

Other products based on phosphoric esters containing perfluoropolyether chains to confer oleo-repellence to paper both for the wet-end and size-press treament are also known. See for example European patent applications No. 03.000.384, 03.000.385. The two kinds of treatment require different formulations when said compounds are used. In said patent applications it is not said if the papers sized with aqueous compositions of said phosphates are capable to satisfy the most severe above tests used by paper mills, as, for example, the resistance tests to fat acid mixtures and to trementine.

Tests carried out by the Applicant have shown that papers sized with said phosphates do not pass most of said tests. To pass the above tests it needs to use a remarkable amount of phosphates bringing a cost rising hardly bearable by paper mills.

The need was therefore felt to find compounds capable to confer to paper substrata, both in size-press and in wet-end treatment, a very good oleo-repellence such to satisfy the most severe resistance tests, for example the Ralston Crease Test, the resistance to oleic acid and to fat acid mixtures, using reduced amounts of compound with respect to those used with the compounds of the prior art. Said reduced amounts render the treatment costs suitable to the application.

Compounds capable to solve said technical problem have now been surprisingly found.

An object of the present invention are carboxylic acids comprising perfluoropolyether chains, of formula:

$$T_1-CFW_1-O-R_f-CFW_2-T_2 \qquad (I)$$

wherein

T$_1$, T$_2$, equal to or different from each other, are selected from the group formed by —CH$_2$—B—Y—(COOH)$_n$, —CH(CF$_3$)O—Y(COOH)$_n$, —F, —CF$_3$, —C$_2$F$_5$, —(C$_2$F$_4$)Cl; B═O—or —S—; Y represents a C$_1$-C$_{20}$ alkylene chain, optionally containing heteroatoms as O, N, S; n is an integer between 1 and 4; with the proviso that at least one of the two end grups T$_1$, T$_2$ is —CH$_2$—B—Y—(COOH)$_n$, —CH(CF$_3$)O—Y(COOH)$_n$;

W$_1$, W$_2$, equal to or different from each other, are —F or —CF$_3$;

R$_f$ is a (per)fluoropolyoxyalkylene chain formed of one or more repeating units, statistically distributed along the chain, having the following structure: (CFXO), (CF$_2$CF$_2$O), (CF$_2$CF$_2$CF$_2$O), (CF$_2$CF$_2$CF$_2$CF$_2$O), (CR$_4$R$_5$CF$_2$CF$_2$O), (CF(CF$_3$)CF$_2$O), (CF$_2$CF(CF$_3$)O), wherein X=F, CF$_3$; R$_4$ and R$_5$, equal to or different from each other, are selected from H, Cl, or perfluoroalkyl from 1 to 4 carbon atoms, said Rf having a number average molecular weight in the range 500-10,000, preferably 800-3,000.

In said carboxylic acids, the carboxyl is bound to the (per)fluoropolyether chain by an alkylene containing one O or S atom.

The preferred perfluoropolyether chain R$_f$ is selected from the following structures:

(A) —(CF$_2$CF(CF$_3$)O)$_a$(CFXO)$_b$—wherein X is F or CF$_3$; a and b are integers such that the number average molecular weight is within the above range; a/b is between 10 and 100; or the repeating units in (A) can be linked as follows: —(CF$_2$CF(CF$_3$)O)$_a$(CFXO)$_b$—CF$_2$(R'$_f$) CF$_2$—O—(CF$_2$CF(CF$_3$)O)$_a$(CFXO)$_b$—wherein R'$_f$ is a fluoroalkylene group from 1 to 4 C atoms;

(B) —(CF$_2$CF$_2$O)$_c$(CF$_2$O)$_d$(CF$_2$(CF$_2$)$_z$O)$_h$—wherein c, d and h are integers such that the number average molecular weight is within the above mentioned range; c/d is between 0.1 and 10; h/(c+d) is between 0 and 0.05; z is 2 or 3; h can also be equal to 0;

(C) —(C$_3$F$_6$O)$_e$(CF$_2$CF$_2$O)$_f$(CFXO)$_g$—wherein X is F or CF$_3$; e, f, g are integers such that the number average molecular weight is within the above range; e/(f+g) is between 0.1 and 10, f/g is between 2 and 10; (C$_3$F$_6$O) can represent units of formula —(CF$_2$CF—(CF$_3$)O) or —(CF(CF$_3$)CF$_2$O)—;

(D) —(CF$_2$(CF$_2$)$_z$O)$_s$—wherein s is an integer such to give the above molecular weight, z has the already defined meaning;

(E) —(CR$_4$R$_5$CF$_2$CF$_2$O)$_{j'}$— or —(CR$_4$R$_5$CF$_2$CF$_2$O)$_{p'}$—R'$_f$—O—(CR$_4$R$_5$CF$_2$CF$_2$O)$_{q'}$— wherein R$_4$ and R$_5$ are equal to or different from each other and selected from H, Cl or perfluoroalkyl having from 1 to 4 C atoms; R'$_f$ is a fluoroalkylene group from 1 to 4 C atoms; j', p' and q' are integers such as to have a molecular weight as that above indicated;

(F) —(CF(CF$_3$) CF$_2$O)$_{j''}$—(R'$_f$)—O—(CF(CF$_3$)CF$_2$O)$_{j''}$ j'' being an integer such to give the above molecular weight, R''$_f$ is a fluoroalkylene group having from 1 to 4 C atoms.

Particularly preferred structures are (A) and (B).

Particularly preferred compounds of formula (I) are those having formula:

HOOCCH$_2$OCH$_2$CF$_2$O(CF$_2$CF$_2$O)$_c$(CF$_2$O)$_d$CF$_2$CH$_2$OCH$_2$COOH wherein c/d ranges from 0.1 to 10, preferably from 1 to 5.

A further object of the present invention is a process to obtain the carboxylic acids of formula (I). Said process comprises the following steps:

a) reaction of an alcohol having a perfluoropolyoxyalkylene formula

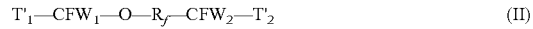

$$T'_1\text{—CFW}_1\text{—O—}R_f\text{—CFW}_2\text{—T'}_2 \qquad (II)$$

wherein R$_f$, W$_1$ and W$_2$ have the above meanings; T'$_1$ and T'$_2$, equal to or different from each other, represent an end group —O—CH$_2$OH, —O—CH$_2$SH, —CH(OH)CF$_3$, —F, —CF$_3$, —C$_2$F$_5$, —(C$_2$F$_4$)Cl with the proviso that at least one of the two end groups T'$_1$ and T'$_2$ be equal to —O—CH$_2$OH, —O—CH$_2$SH or —CH(OH)CF$_3$; with an organic or inorganic base, in a ratio of base equivalents with respect to the fluorinated alcohol in the range 1.1-2, preferably 1.2-1.5, at a temperature in the range 20° C.-100° C., preferably 40° C.-80° C. to obtain the alcoholate;

b) reaction of the mixture obtained in step a) comprising the alcoholate of the compound (II) with a compound of general formula

$$Z\text{—Y(COOR)}_n \qquad (III)$$

wherein Y has the meaning indicated for formula (I), Z=Cl, Br, I, —O—SO$_2$—Ph—CH$_3$, R=C$_1$-C$_5$ linear or branched alkyl group, at a temperature in the range 20° C.-100° C., preferably 40° C.-80° C., using ratios between the alcoholate equivalents and the compound (III) between 1:1 and 1:2, preferably between 1:1.2 and 1:1.6;

c) hydrolysis of the product obtained in step b) at room temperature by addition of an alkaline aqueous solution and subsequent heating up to 80° C., under stirring;

d) acidification of the reaction mixture obtained in c) obtaining an organic phase and an aqueous phase from which the organic phase formed of the compound of formula (I) is separated.

Alternatively, in step b), instead of the compound (III), carboxylic acid salts of formula:

$$Z\text{—Y(COO}^-\text{M}^+)_n \qquad (IV)$$

can be used, wherein Y, Z and n have the above meaning; M=Li, Na, K. The obtained product is successively treated as described in step d). In this alternative process, wherein the compound (IV) is used, the hydrolysis step c) is not necessary.

In step a) an organic or inorganic base can be used, for example potassium terbutylate, KOH, tertiary amines, potassium carbonate can be mentioned.

It is also possible to use a solvent for the fluorinated alcohol which is inert under the reaction conditions, as for example terbutyl alcohol, acetonitrile, diglyme.

In step b) the compounds of formula (III) or (IV) can be added to the mixture obtained in step a) in a single portion or in more portions. The reaction times are generally comprised between 4 and 15 hours in connection with the reaction temperature and with the optional solvent used.

In step d) the acidification is carried out with an aqueous solution of an inorganic acid, and the separated organic phase is washed with acidulated water and then dried by heating so to remove the water and the possible solvent.

The precursors of formula (II) can for example be obtained according to the teaching of U.S. Pat. No. 3,810,874 applied to the above perfluoropolyether structures.

The products of formula (I) can be used under an acid form or under a salified form.

The salts are obtained by neutralization of the acids of formula (I) with bases, as, for example, alkaline metal hydroxides or primary, secondary and tertiary amine. Preferred examples of bases are: primary, secondary, tertiary amines as for example methyl amine, diethyl amine, triethyl amine, ethanolamine, diethanolamine, triethanolamine, morpholine and others.

The acids of formula (I) and their salts are used under the form of aqueous dispersions, optionally in the presence of a solvent, for the above mentioned oleo-repellence applications.

A further object of the invention are aqueous compositions containing from 0.01% to 30% by weight, preferably from 0.1% to 10% by weight, of acids of formula (I) or their salts, optionally containing a solvent of the acid or of the salt selected from aliphatic alcohols having from 2 to 6 carbon atoms, or aliphatic glycols having from 2 to 8 carbon atoms, optionally having an etherified hydroxylic group, or ketones or esters having from 3 to 10 carbon atoms.

The compounds and the compositions of the invention are preferably used in the oleo-repellent paper sizing in size-press and wet-end applications, preferably in wet-end applications.

The wet-end process consists in the paper sizing in mass with the invention compositions starting from a cellulose slurry in water. The slurry can be formed or of virgin, soft or hard wood, treated with sulphate and/or sulphite, suitably refined, or of recycled cellulose slurries or also by mixtures of said two kinds of slurries. The dry cellulose concentration in the slurry ranges from 0.1% to 10% by weight. The pulp slurry can contain the additives normally used in the paper industry, for example organic or inorganic fillers, as talc, kaolin, calcium carbonate or titanium dioxide; coadjuvant agents as starches, dextrins, retention agents, flocculating agents, buffer systems, fungicides, biocides, sequestrants, glue agents as ASA (alkenyl succinic anydride) or AKD (alkyl ketene dimer). The cellulose suspension can have both acid and basic pH, preferably basic.

Usually the invention compositions are added to the cellulose aqueous slurry in an amount such to obtain paper having a content of acid of formula (I) or its salt ranging from 0.2% to 5% by weight based on the dry cellulose.

To improve the product retention on the cellulose fibers, it is preferable to add to the paper slurry a fixative agent before sizing. Said fixative agent is generally a cationic compound, generally of polymeric nature, having a molecular weight ranging from 10,000 to 5,000,000, in an amount ranging from 0.01% to 1% by weight of cationic compound based on the dry cellulose. The fixative agents are for example the following: cationic polyacrylamides, polyamines, polyamidoamine-epichlorohydrin or dimethylamine-epichlorohydrin copolymers, polyethylenimines, polydiallyl-dimethyl-ammonium chloride. To the pulp slurry chelants can be added to moderate the water hardness.

After the addition of the invention composition to the cellulose slurry, the water is removed obtaining a wet paper which is dried, for example, at temperatures in the range 90° C.-130° C., according to the standard procedures used in the paper industry.

The size-press process consists in the paper external sizing to confer oleo-repellence thereto by a roll system (size-press) applying the treating composition on both sides of the preformed paper.

It is to be noted that in both applications the invention compounds allow to obtain oleo-repellence values much more adherent to the real requirements since they pass the above-application tests. Furthermore, in comparison with the compounds of the prior art, said results are obtained by applying a much lower amount of compound.

The following Examples illustrate the invention without limiting the scope thereof.

EXAMPLES

Oleo-Repellence Evaluation

The oleo-repellence evaluation has been carried out by the following tests:

Kit Test (KT)

This test follows the TAPPI 557 method referred to 16 solutions having a different concentration of castor oil, toluene and heptane. Said solutions discriminate the various levels of oleo-repellent treatment and therefore assign the respective KIT Test values essentially in function of the surface tension which ranges from 34.5 dine/cm of the solution 1 to 22 dine/cm of the solution 12, to 20.3 dine/cm of the solution 16. The animal or vegetable fats have surface tensions not lower than 24 dine/cm, corresponding to a Kit Test value of about 7.

To the paper sized a Kit Test value is assigned by the following procedure: a paper specimen is placed on a clean flat, black-coloured surface and a drop of the solution 1 is let fall thereon from a height of 25 mm. The drop is left in contact with the paper for 15 seconds, removing it then by clean blotting paper and the surface under the drop is examined. If said surface does not appear dark (halo), the test is repeated using a solution having a lower surface tension, until the presence of a dark halo is observed.

The Kit Test value assigned to the paper is that corresponding to the previous solution which gives rise to the dark halo.

Ralston Crease Test (RP-2 Test)

The reactants and the instruments necessary for this test are available by Ralston Purina® Company. The Ralstone Crease Test allows to evaluate the resistance to the oil penentration in greaseproof papers used in pet-food packaging. The paper specimen to be tested, having 10 cm×10 cm sizes, is conditioned for 24 h at 23° C. and 50±2% of relative humidity. Then the specimen is positioned over a coated paper sheet having the same surface as that of the specimen, on which a grid of 100 small squares is printed. The whole is placed on a flat, smooth and stiff surface.

A metal ring having a diameter of 7.5 cm is put on the paper specimen to be tested. A metal pipe (height=2.5 cm, internal diameter 2.5 cm) is placed in the middle of the specimen, then 5 g of sand (Ottawa sand, 20-30 mesh) are poured into the pipe. The pipe is then removed so to form a sand cone in the middle of the specimen.

Then 1.3 cc of a specific synthetic oil supplied by Ralston Purina which contains 0.1% by weight of a red dye are added to the sand cone by a syringe. Usually for the test at least 4 specimens of the same paper sample are prepared. The specimens with the sand are then placed in a stove at 60° C. and at 50±2% of relative humidity for 24 hours. This time elapsed, the specimens with the sand are removed and the underlying grid surface stained by the oil is evaluated.

The RP-2 Test result is expressed as number of stained small squares, which expresses also the percentage of small squares, which is the average of the results obtained on at least 4 specimens of the same sample.

The sample acceptability limit is 2% of the stained surface.

A similar more severe test (RP-2 with creasing) consists in using a paper sample previously creased along the two diagonals with a suitable roll, having a weight of 2040±45 g, diameter of 9.5 cm and width of 4.5 cm, covered by a rubber layer having a thickness of 0.6 cm. The roll speed during the creasing must be of 2-3 cm/sec.

In this case also the same above acceptability limit is valid.

Resistance Test to Oleic Acid

A paper sized specimen having 10 cm×10 cm sizes is placed in a stove at 60° C. to condition, then ten drops of oleic acid having the same temperature are let fall from a height of 25 mm. The paper specimen is thus left in the stove for 2 hours at 60° C. The test time elapsed, the paper specimen is taken off from the stove and the oil drops are removed, visually evaluating the paper as in the above test.

The test is considered positive when the paper shows no halos either on the side sized or on the opposite side.

Resistance Test to Fat Acids Mixtures

Five mixtures of free fat acids are prepared starting from the respective pure compounds. The considered mixtures have the following composition:

| | Mixture (A*) (% by wt) | Mixture (B*) (% by wt) | Mixture (C*) (% by wt) | Mixture (D*) (% by wt) | Mixture (E*) (% by wt) |
|---|---|---|---|---|---|
| Castor oil | 80 | — | — | — | — |
| Oleic Acid C18 | 20 | 75 | 62 | 41 | 9 |
| Linoleic Acid C18 | — | 11 | 4 | 3 | 2 |
| Palmitic Acid C16 | — | 14 | 32 | 38 | 18 |
| Lauric Acid C12 | — | — | 2 | 8 | 56 |
| Capric Acid C10 | — | — | — | 3 | 6 |
| Caprilic Acid C8 | — | — | — | 1 | 8 |
| Caproic Acid C6 | — | — | — | 6 | 1 |

Five vessels each containing the single mixtures of fat acids called (A*), (B*), (C*), (D*), (E*) are placed in a stove kept at 60° C. at least one half before the test, to guarantee composition and temperature uniformity. Said mixtures, in fact, appear at room temperature as waxy solids having a variable melting point.

Ten specimens having 5×5 cm sizes are then cut out for each specimen to be tested. These specimens are placed in a stove at 60° C., paying attention to place them on a dark surface, for example a black card. On each of them a certain number of drops of the test mixture is then placed. At least two specimens are used for each mixture.

At the end of this operation, the stove is closed and the specimens are left in contact with the fluid drops of the test mixture for 10 minutes. This time elapsed, the stove is opened and the mixture drops are removed by blotting paper. The penetration of the fluid of the test mixture in the paper specimen is shown by the darkening of the area below each drop.

For each test mixture, the test is positive if no penetration takes place.

The test result is expressed with the letter of the test mixture preceding the first text mixture which penetrates through the specimen.

Tests carried out by the Applicant have shown that the penetration capability of hot fat acids, at temperatures ranging from 40° C. to 60° C., depends on their chemical structure. In particular, in linear fat acids, their hot penetration capability on papers sized with oleo-repellent products mainly depends on the hydrocarbon chain length, i.e. on the number of carbon atoms of the fat acid. The lower this number, the lower will be the necessary time so that, at constant temperature, fat acid drops penetrate the paper sized.

The Applicant has furthermore found that, at equal number of carbon atoms, the presence of unsaturations in the structure of a linear fat acid does not substantially modify its penetration capability in paper sized specimens, with respect to the same fat acid free from unsaturations.

These considerations are at the basis of the fat acid test for the evaluation of the greaseproof properties. The test implies the contact of the paper sized specimens with oleo-repellent substances with hot fat acid mixtures having a variable composition from (A*) to (E*), so that the average length of the hydrocarbon chains be decreasing.

The mixture (A*) contains 20% by weight of fat acid, diluted in 80% by weight of castor oil. It has a low aggressive power and is used to discriminate the low performance levels, for example those necessary to produce disposable papers for hamburgers, and in general for the fast-food. The papers sized commercially utilized for the aforesaid uses normally have Kit Test values from 3 to 5.

The compositions of the mixtures (B*), (C*), (D*) and (E*) represent respectively the compositions in fat acids of the olive oil, animal lard, butter and coconut oil.

The present test, as regards the short times required for its accomplishment, is a valid alternative to the Kit Test and besides evaluates the paper greaseproof behavior in more realistic terms since it uses the fat acids. present in the triglycerides contained in the common fats and oils.

Resistance Test to Trementine (Turpentine Test TAPPI T454 om-00)

5 grams of Ottawa sand are weighed and by a funnel they are placed on the paper sized specimen having about 10×10 cm sizes positioned in its turn on a coated paper white sheet. The funnel must have the stem horizontally cut so that the sand be conically placed on the specimen. On the sand cone top 1.1 ml of coloured trementine (about 1% of red dye) are let drop by graduated pipette. The test time is timed. For the first 5 minutes the paper specimen is moved every minute from the underlying sheet and the possible trementine stains are observed on the white paper sheet which serves as a marker. After the first 5 minutes, this operation is carried out every 5-10 minutes up to a maximum of 30 minutes.

The test is positive when after 30 minutes no stain on the underlying white sheet is noticed.

Resistance Test to Exhausted Seed-oil (Hot Mazola Oil Test)

This test is used in Europe for packaging paper sized for fast food having a low Kit Test value ranging from 3 to 6. The paper sized specimen, placed on an underlying black paper sheet is put in a stove at 110° C. and then 1 ml of exhausted seed-oil is placed thereon, starting to time the test time which lasts 20 minutes. At regular intervals it is observed if the oil is absorbed by the specimen, shown by the darkening of the oil stain which, making the paper to become transparent, shows the black of the underlying paper sheet. If the stain is shown before 20 minutes being elapsed, the test is interrupted and the elapsed time is recorded.

If within 20 minutes no black stain is noticed, then the percentage of superficially absorbed oil is calculated by differential weight, i.e. weighing the paper specimen with the deposited oil and weighing it again after removal of the surface oil with blotting paper.

The test result is considered positive if within 20 minutes no stain of the absorbed oil is shown.

Example 1

Preparation of the Compound of Formula

HOOCCH$_2$OCH$_2$CF$_2$O(CF$_2$CF$_2$O)$_c$(CF$_2$O)$_d$CF$_2$CH$_2$OCH$_2$COOH starting from ClCH$_2$COONa 40 g of terbutyl alcohol and 19 g (0.17 moles) of potassium terbutylate are fed into a 500 ml glass reactor equipped with mechanical stirrer, thermometer and condenser. Then 100 g (0.13 eq) of HOCH$_2$CF$_2$O(CF$_2$CF$_2$O)$_c$(CF$_2$O)$_d$CF$_2$CH$_2$OH (EW=751) wherein c/d=2 are fed under stirring at room temperature. The reaction mixture is stirred for about 30 minutes, then 19.7 g (0.17 moles) of ClCH$_2$COONa are fed into the reactor. The so obtained mixture is heated at 80° C. and kept under stirring for about 12 hours. After cooling, 200 g of an HCl aqueous solution at 10% by weight are added. The phases are then let separate and the heavy organic phase is separated and washed with 200 g of an HCl aqueous solution at 10% by weight. After separation, the organic phase is anhydrified by stripping at 100° C. at a residual pressure of 10$^{-2}$ mbar for about 4 hours. 103 g of product having a yield equal to 96% are thus obtained. The IR and NMR analyses ($^1$H, $^{19}$F and $^{13}$C) confirm the structure of the above product.

Example 2

Preparation of the Derivative of Formula
HOOCCH$_2$OCH$_2$CF$_2$O(CF$_2$CF$_2$O)$_c$(CF$_2$O)$_d$CF$_2$CH$_2$OCH$_2$COOH from ClCH$_2$COOEt 40 g of terbutyl alcohol and 19 g (0.17 moles) of potassium terbutylate are fed into a 500 ml glass reactor equipped with mechanical stirrer, thermometer and condenser. Then 100 g (0.13 eq) of HOCH$_2$CF$_2$O(CF$_2$CF$_2$O)$_c$(CF$_2$O)$_d$CF$_2$CH$_2$OH (EW=751) wherein c/d=2 are fed under stirring at room temperature. The reaction mixture is stirred for about 30 minutes, then 20.7 g (0.17 moles) of ClCH$_2$COOEt are fed into the reactor. The so obtained mixture is heated at 80° C. and kept under stirring for about 8 hours. 200 g of a KOH aqueous solution at 30% by weight are then added to the mixture by dropping. The mixture is kept at 80° C. under stirring for about 3 hours. After cooling a HCl aqueous solution at 37% by weight is added until reaching an acid pH (pH=1-2). The phases are then let separate and the heavy organic phase is separated and washed with 200 g of a HCl aqueous solution at 10% by weight. After separation, the organic phase is anhydrified by stripping at 100° C. at a residual pressure of 10$^{-2}$ mbar for about 4 hours. 99.3 g of product with a yield equal to 92% are thus obtained. The IR and NMR analyses ($^1$H, $^{19}$F and $^{13}$C) confirm the structure of the above product.

Example 3

3 aqueous compositions have been prepared containing respectively:

| | | |
|---|---|---|
| A) | compound of the Example 1 | 20% w/w |
| | NH$_4$OH | 0.6% w/w |
| | H$_2$O | complement to 100 |
| B) | compound of the Example 1 | 20% w/w |
| | NH$_4$OH | 0.6% w/w |
| | Dipropylenglycol monomethylether (DPM) | 3% w/w |
| | H$_2$O | complement to 100 |
| C) | compound of the Example 1 | 20% w/w |
| | Triethylamine (TEA) | 4% w/w |
| | H$_2$O | complement to 100 |

Wet-End Treatment (in Mass)

Examples 4-6

Two slurries of virgin cellulose fiber are prepared, which are refined at 28° SR and 32° SR (Shopper degrees), determined according to the ATICELCA MC 201-76 method corresponding to the UNI 7621-76 standard, cationized with 0.4% of NALCO 7607 (cationic retentive agent). Samples of each slurry are sized with the compositions A, B or C prepared in the Example 3 so as to have paper specimens having a content by weight of fluorinated compound of the Example 1 based on the dry cellulose as indicated in the Examples of Table 1. The drying of the paper specimen has been carried out at 105° C.

The paper is subjected to calendering by passage between two cylinders heated at 110° C., among which a pressure of 200 bar (20 MPa) is achieved.

The values obtained for the various tests in function of the % by weight of the fluorinated compound of the Example 1 are indicated in Table 1.

It is noticed that the values obtained in the various tests result independent from the paper refining degree.

Examples 7-7a (Comparative)

The procedure of the Examples 4-6 is repeated, but by using two dispersions of anionic polyurethane obtained according to the Example 1 of European patent application No. 02.014.155 starting from a (per)fluoropolyether diol having formula HOCH$_2$CF$_2$(OCF$_2$CF$_2$)$_p$(OCF$_2$)$_q$OCF$_2$CH$_2$OH wherein p/q=2 and number average molecular weight 1,500, from isophorondiisocyanate, dimethylpropionic acid and triethylamine, by treating the cellulose slurry so to have a final amount of polyurethane equal to 0.7% (Example 7) and to 0.45% (Example 7a) by weight based on the dry fiber.

The application tests have shown the oleo-repellent performances indicated in Table 1.

Examples 8-8a (Comparative)

The procedure of the Examples 4-6 is repeated, but by using two aqueous formulations (pH=9), containing a mixture of phosphates formed of 85% by moles of a phosphate of structure (OH)$_m$(O$^-$Z$^+$)$_{2-m}$P(O) [O—L—YFC—O—R$_f$—CFY—L—O—P(O)(O$^-$Z$^+$)]$_{m'}$—[O—L—YFC—O—R$_f$—CFY—L—O]P(O)(O$^-$Z$^+$)$_{2-m}$(OH)$_m$    (B)

wherein m'=0 and of 25% by moles of the phosphate of structure B) wherein m'=2, both having $Z=NH_4^+$; $L=-CH_2-CH_2(OCH_2CH_2)_n-$ with n=2; m=0,5; Y=F; $R_f$ comprising repeating units of $-(CF_2O)_{a'}-(CF_2CF_2O)_{b'}-$ type with a'/b'=0.5 and having number average molecular weight of 1,400, 20% by weight of tetrahydrofuran (THF).

The slurries result to contain respectively 0.7% by weight of phosphate based on the dry cellulose (Example 8) and 0.45% (Example 8a) by weight based on the dry fiber.

The application tests have shown the oleo-repellent performances indicated in Table 1.

Size Press Treatment

Examples 9-17

The formulations A, B, C, of the Example 3 have been deposited respectively on the cylinders of a size press machine with which filter paper sheets have been sized having a paper weight of 65 g/m², by passage through the rolls at the pressure of 3 bar. Then each paper sheet has been dried on a roll heated at 105° C.

The application tests have shown the oleo-repellent performances indicated in Table 2.

Example 18 (Comparative)

A paper support having a paper weight of 65 g/m² is treated in a size-press machine at room temperature. The pressure between the cylinders is 3 bar (3.10⁵ Pa). An aqueous dispersion containing 1% by weight of the anionic polyurethane of the Example 7 (comparative) is used. After the treatment the paper is dried in press at 105° C. The application tests have shown the oleo-repellent performances indicated in Table 2.

Example 19 (Comparative)

An aqueous formulation (pH=7) has been prepared containing 20% by weight of a phosphate mixture formed of 85% by moles of a phosphate of structure (B)

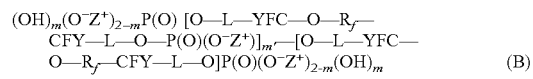

(B)

wherein m'=0 and of 25% by moles of the phosphate of structure B) wherein m'=1, both having $Z=NH_4^+$; m=1; $L=-CH_2-CH_2(OCH_2CH_2)_n-$ with n=2; Y=F; $R_f$ comprising repeating units of $-(CF_2O)_{a'}-(CF_2CF_2O)_{b'}-$ type with a'/b'=0.5 and having number average molecular weight of 1,400, and 8.5% by weight of dipropylenglycol monomethylether.

The formulation has been diluted with water until having 0.6% by weight of phosphate and then deposited on the cylinders of a size-press machine by which a paper sheet having a paper weight of 65 g/m² has been sized by passage through the rolls at the pressure of 3 bar. Then it has been dried on a roll heated at 105° C. The application tests have shown the oleo-repellent performances indicated in Table 2.

TABLE 1

Wet-end treatment

| Example | Composition | % by weight of fluorinated product (based on dry cellulose) | KIT Test | RP-2 Test | Oleic acid test | Fat acid mixture test | Trementine test | Exhausted seed-oil test |
|---|---|---|---|---|---|---|---|---|
| 4 | A | 0.5 | 9-10 | 0(*) | Positive | D* | Positive | Positive |
| 5 | B | 0.45 | 8-9 | 0 | Positive | D* | Positive | Positive |
| 6 | C | 0.45 | 9 | 0(*) | Positive | C* | Positive | Positive |
| 7 (comp) | — | 0.7 | 7 | 0 | Negative | B* | Positive | Positive |
| 8 (comp) | — | 0.7 | 7 | 0(*) | Positive | C* | Positive | Positive |
| 7a (comp) | — | 0.45 | 6 | 3-4 | Negative | Negative | Negative | Positive |
| 8a (comp) | — | 0.45 | 6 | 5-6 | Negative | A* | Negative | Positive |

(*) RP-2 with creasing

TABLE 2

Size-press treatment

| Example | Composition | % by weight of fluorinated product | KIT Test | RP-2 Test | Trementine test | Exhausted seed-oil test |
|---|---|---|---|---|---|---|
| 9 | A | 0.3 | 8 | 0 | Positive | Positive |
| 10 | A | 0.4 | 10 | 0(*) | Positive | Positive |
| 11 | B | 0.2 | 8 | 0 | Positive | Positive |
| 12 | B | 0.3 | 9-10 | 0 | Positive | Positive |
| 13 | B | 0.4 | 10 | 0(*) | Positive | Positive |
| 14 | C | 0.2 | 8 | 0 | Positive | Positive |
| 15 | C | 0.3 | 9-10 | 0(*) | Positive | Positive |
| 16 | C | 0.4 | 10 | 0(*) | Positive | Positive |
| 17 | C | 0.5 | 10 | 0(*) | Positive | Positive |
| 18 (comp) | — | 1 | 7 | 0 | Positive | Positive |
| 19 (comp) | — | 0.6 | 8 | 0(*) | Positive | Positive |

(*) RP-2 with creasing

The invention claimed is:

1. A method for conferring oleorepellence to paper substrata in wet-end and size-press applications comprising the step of sizing with compounds of the formula:

$$T_1-CFW_1-O-R_{f-CFW2}-T_2 \quad (I)$$

or salts thereof, wherein $T_1$, $T_2$, equal to or different from each other, are selected from the group formed of $-CH_2-B-Y-(COOH)_n$, $-CH(CF_3)O-Y(COOH)_n$, $-F$, $-CF_3$, $-C_2F_5$, $-(C_2F_4)Cl$; $B=-O-$ or $-S-$;

Y represents a $C_1-C_{20}$ alkylene chain, optionally containing heteroatoms as O, N, S; n is an integer between 1 and 4; with the proviso that at least one of the two end groups $T_1$, $T_2$ is $-CH_2-B-Y-(COOH)_n$, $-CH(CF_3)O-Y-(COOH)_n$;

$W_1$, $W_2$, equal to or different from each other, are $-F$ or $-CF_3$;

$R_f$ is a (per)fluoropolyoxyalkylene chain formed of one or more repeating units, statistically distributed along the chain, having the following structure:

(CFXO), $(CF_2CF_2O)$, $(CF_2CF_2CF_2O)$, $(CF_2CF_2CF_2CF_2O)$, $(CR_4R_5CF_2CF_2O)$, $(CF(CF_3)CF_2O)$, $(CF_2CF(CF_3)O)$, wherein $X=F$, $CF_3$; $R_4$ and $R_5$, equal to or different from each other, are selected from H, Cl, or perfluoroalkyl from 1 to 4 carbon atoms, said $R_f$ having a number average molecular weight in the range 500-10,000.

2. A method for conferring oleorepellence to paper substrata in wet-end and size-press, comprising the step of sizing with aqueous compositions containing from 0.01% to 30% by weight, of compounds of formula (I) or salts thereof according to claim 1, optionally containing a solvent selected from aliphatic alcohols having from 2 to 6 carbon atoms, aliphatic glycols having from 2 to 8 carbon atoms, optionally having an etherified hydroxylic group, ketones or esters having from 3 to 10 carbon atoms.

3. A method according to claim 1, wherein $R_f$ has a number average molecular weight in the range of 800-3,000.

4. A method according to claim 1, wherein Rf is selected from the following structures:

(A) $-(CF_2CF(CF_3)O)_a(CFXO)_b-$ wherein X is F or $CF_3$; a and b are integers such that the number average molecular weight is within the above range; a/b is between 10 and 100;

or the repeating units in (A) can be linked as follows:

$-(CF_2CF(CF_3)O)_a(CFXO)_b-CF_2(R'_f)CF_2-O-(CF_2-O-(CF2CF(CF_3)O)_a(CFXO)_b-$ wherein $R'_f$ is a fluoroalkylene group from 1 to 4 C atoms;

(B) $-(CF_2CF_2O)_c(CF_2O)_d(CF_2(CF_2)_zO)_h-$ wherein c, d and h are integers such that the number average molecular weight is within the above range; c/d is between 0.1 and 10; h/(c+d) is between 0 and 0.05; z is 2 or 3; h can also be equal to 0;

(C) $-(C_3F_6O)_e(CF_2CF_2O)_f(CFXO)_g-$ wherein X is F or $CF_3$; e, f, g are integers such that the number average molecular weight is within the above range; e/(f+g) is between 0.1 and 10, f/g is between 2 and 10; $(C_3F_6O)$ can represent units of formula $-(CF_2CF(CF_3)O)$ or $-(CF(CF_3)CF_2O)-$;

(D) $-(CF_2(CF_2)_zO)_s-$ wherein s is an integer such to give the above mentioned molecular weight, z has the already defined meaning;

(E) $-(CR_4R_5CF_2O)_{j'}-$ or
$-(CR_4R_5CF_2O)_p$, $R'_f-O-(CR_4R_5CF_2CF_2O)_{q'}-$ wherein $R_4$ and $R_5$ are equal to or different from each other and selected from H, Cl or perfluoroalkyl having from 1 to 4 C atoms; $R'_f$ is a fluoroalkylene group from 1 to 4 C atoms; j', p' and q' are integers such to have a molecular weight as that above indicated;

(F) $-(CF(CF_3)CF_2O)_{j''}-(R'_f)-O-(CF(CF_3)CF_2O)_{j''}$ j" being an integer such to give the above molecular weight, $R'_f$ is a fluoroalkylene group having from 1 to 4 C atoms.

5. A method according to claim 4, wherein $R_f$ has the structure (A) or (B).

6. A method according to claim 1, wherein the compounds have the formula:

$$HOOCCH_2OCH_2CF_2O(CF_2CF_2O)_c(CF_2O)_dCF_2CH_2OCH_2COOH$$

wherein c/d ranges from 0.1 to 10.

7. A method according to claim 6, wherein c/d ranges from 1 to 5.

8. A method according to claim 1, wherein salts of the compounds of formula (I) are used.

9. A method according to claim 2, wherein the aqueous compositions contain from 0.1% to 10% by weight of the compounds.

the following is an examiner's statement of reasons for allowance:

the outstanding rejections under section 112, second paragraph and 101 are withdrawn in view of the amendments reciting positive steps in the claims;

an updated search failed to uncover a reference that teaches a method of conferring oleorepellance to paper substrata comprising a step of sizing with the compounds of formula (I).

the updated search also failed to uncover a reference that would have motivated those of ordinary skill to modify its disclosure to include a step of sizing with the compounds of formula (I).

* * * * *